(12) United States Patent
Schecter

(10) Patent No.: US 7,751,889 B1
(45) Date of Patent: Jul. 6, 2010

(54) CLOSED LOOP PROGRAMMING FOR INDIVIDUAL ADJUSTMENT OF ELECTRO-MECHANICAL SYNCHRONY

(75) Inventor: Stuart O. Schecter, Great Neck, NY (US)

(73) Assignee: Pacesetter, Inc., Sylmar, CA (US)

( * ) Notice: Subject to any disclaimer, the term of this patent is extended or adjusted under 35 U.S.C. 154(b) by 251 days.

(21) Appl. No.: 11/734,117

(22) Filed: Apr. 11, 2007

(51) Int. Cl.
*A61N 1/365* (2006.01)

(52) U.S. Cl. .............................. 607/17; 607/9; 607/11; 600/9; 600/10; 600/11

(58) Field of Classification Search .............. 600/509, 600/513, 300, 314, 315, 484; 607/2–4, 10–11, 607/18, 20, 24, 116–122
See application file for complete search history.

(56) References Cited

U.S. PATENT DOCUMENTS

| | | | | |
|---|---|---|---|---|
| 5,549,650 A * | 8/1996 | Bornzin et al. | ................. | 607/24 |
| 5,620,473 A * | 4/1997 | Poore | .......................... | 607/27 |
| 5,836,987 A * | 11/1998 | Baumann et al. | ............... | 607/17 |
| 6,751,503 B1* | 6/2004 | Kroll | ........................... | 607/18 |
| 7,010,347 B2* | 3/2006 | Schecter | ...................... | 607/17 |
| 7,260,431 B2* | 8/2007 | Libbus et al. | .................. | 607/4 |
| 7,426,412 B1* | 9/2008 | Schecter | ...................... | 607/20 |
| 2004/0049235 A1* | 3/2004 | Deno et al. | ..................... | 607/9 |
| 2004/0059237 A1* | 3/2004 | Narayan et al. | ............. | 600/509 |
| 2004/0127804 A1* | 7/2004 | Hatlesad et al. | ............. | 600/513 |
| 2004/0172079 A1* | 9/2004 | Chinchoy | .................... | 607/17 |
| 2004/0186524 A1* | 9/2004 | Chinchoy | .................... | 607/17 |
| 2004/0220636 A1* | 11/2004 | Burnes | ........................ | 607/17 |
| 2005/0027322 A1* | 2/2005 | Warkentin | ................... | 607/17 |
| 2005/0043895 A1* | 2/2005 | Schechter | ...................... | 702/19 |
| 2005/0182447 A1* | 8/2005 | Schecter | ....................... | 607/2 |
| 2005/0192506 A1* | 9/2005 | Kim et al. | .................... | 600/510 |
| 2006/0041276 A1* | 2/2006 | Chan | ............................ | 607/3 |
| 2006/0161208 A1* | 7/2006 | Pastore et al. | ................. | 607/17 |
| 2006/0253162 A1* | 11/2006 | Zhang et al. | .................. | 607/26 |
| 2007/0191901 A1* | 8/2007 | Schecter | ...................... | 607/17 |
| 2008/0262361 A1* | 10/2008 | Gutfinger et al. | ............ | 600/486 |
| 2009/0062667 A1* | 3/2009 | Fayram et al. | .............. | 600/486 |

* cited by examiner

*Primary Examiner*—Carl H Layno
*Assistant Examiner*—Paula J Stice

(57) ABSTRACT

An implantable therapy system including implantable stimulation and control components. The implantable components operate under a set of variable parameters that can be adjusted for improved performance for an individual patient. The implantable components are adapted to self-evaluate the patients physiologic performance and autonomously adjust an existing set of parameters to improve performance throughout an implantation period without requiring intervention of a clinician, for example with a physicians programmer. The implantable components can compare a patient's exhibited activity to a desired template of that activity to determine when adjustments are indicated. The template can be based on observations of one or more third parties exhibiting normal activity. The implantable components can adjust the operating parameters to improve synchrony of multiple heart chambers and/or to increase a peak contractility.

16 Claims, 7 Drawing Sheets ial patient. In one embodiment, the systems and methods provide a closed loop adaptive programming capability for an implantable therapeutic device. In one embodiment, the implantable device includes interconnected sensors which sense physiologic parameters and the therapeutic device self-adjusts variable parameters to better adapt the therapy provided to the individual patient. In some embodiments, the device varies operation in a plurality of test parameters, evaluates the parameters and self-adjusts operating parameters. This provides the advantages of improving individual adaptation of an implantable therapy device, reducing burdens on the clinician, as well as more timely adjustments of the device as compared to waiting for the next follow up clinical visit.

CLOSED LOOP PROGRAMMING FOR INDIVIDUAL ADJUSTMENT OF ELECTRO-MECHANICAL SYNCHRONY

BACKGROUND OF THE INVENTION

1. Field of the Invention

The invention relates to the field of implantable cardiac stimulation devices and to improved systems and methods of adjusting implantable devices for individual patients.

2. Description of the Related Art

Numerous patients suffer from disease conditions that affect their cardiac performance. For example, diseased myocardium reduces the mechanical pumping capabilities of the heart. Impaired conduction and/or abnormalities in intrinsic activation can result in inappropriate/impaired stimulation of the cardiac tissue.

Implantable cardiac stimulation devices have been developed to provide therapy for at least some patients suffering impaired cardiac function. Implantable cardiac stimulation devices generally include an implantable stimulation pulse generator and a microprocessor based controller regulating operation of the device. Implantable cardiac stimulation devices also typically include one or more implantable leads which are configured for implantation to extend adjacent the patient's heart. The implantable leads typically include one or more electrodes. The electrodes can be configured for dedicated sensing or delivery of stimulation or can be configured for combined sensing and stimulation delivery functions. The implantable devices are generally adapted to automatically sense the patient's status and automatically generate and deliver stimulation for cardiac abnormalities.

One particular category of implantable cardiac stimulation devices are capable of what is generally known as cardiac resynchronization therapy (CRT). CRT capable devices include leads adapted for delivery of therapeutic stimulation to multiple chambers of the patient's heart, such as to the left and right ventricles. CRT devices attempt to improve pumping efficiency of the patient's heart by providing therapeutic stimulation to improve relative synchrony of operation, e.g., contraction/relaxation, between multiple chambers of the patient's heart. For at least certain patient's, CRT can significantly improve an impaired cardiac output and provide corresponding improvements in quality of life.

An expanding patient population with unhealthful lifestyle histories and/or predisposition to cardiac abnormalities contributes to an ever-increasing patient population with impaired cardiac function. Ongoing developments in therapeutic device design provide increased capabilities for the devices thereby expanding the proportion of the patient population that can benefit from therapies available with the devices. The combination of an increasing population in need of cardiac therapy with therapeutic devices capable of providing an increasing variety of therapies results in an increasing number of matches between patients having need of therapy and therapy devices capable of addressing that need.

While this has obvious benefits to public health, there remains a significant burden on attending clinicians in providing appropriate therapy to the individual patients. Implantable cardiac stimulation devices generally include a variety of operational parameters that are preferably adjusted for the particular needs and condition of a given patient. While these variable parameters can be preset, for example to an average setting, in many applications it is preferred that the device as implanted in the patient be evaluated and the operational parameters be adjusted for improved performance in that individual patient.

Accordingly, implantable cardiac stimulation devices are frequently provided with the ability to telemetrically communicate with an external device, such as a physician's programmer. The physician's programmer allows a clinician to communicate with the therapeutic device in the implanted state at time of implantation as well as subsequently during follow-up visits. Such implantable stimulation devices and physicians programmers share bidirectional communication such that the implantable device can upload data to the physician's programmer, such as operational status information and historical data. The physician's programmer can provide commands to the implanted device, for example to adjust the device programming. This allows a skilled clinician to evaluate the operation of the device in the implanted environment and make any indicated adjustments in the device's programming to improve the delivery of therapy to the patient.

While this improves delivery of therapy to the patient, it places a significant burden on the attending clinicians to individualize or optimize the programming of an implantable device with the unique needs and conditions of an individual patient. As devices become more complex with increased capabilities, there is a tendency for an increasing number of parameters that can be individually adjusted for a given patient. Evaluating even a limited number of different combinations of variable parameters with the time needed for designating changes between the different combinations and for the changes to take effect for evaluation can require a significant amount of time from the highly trained and skilled clinician. Thus, it will be appreciated that reducing the burden on highly trained and skilled clinicians in adjusting a therapeutic device for the needs of an individual patient while maintaining the benefits of improvements in available therapeutic systems would be highly desired.

A further issue in adjusting an implantable therapeutic device for treatment of an individual patient is that a patient's condition can be subject to change over time. For example, a patient's condition may deteriorate indicating an adjustment in their therapy regimen. Similarly, a patient's condition can improve such that previously provided therapeutic parameters are no longer appropriate for the approved condition. For example, a patient provided with CRT may positively respond in a phenomena sometimes known as remodeling thereby indicating changes in their therapy. Secondary factors, such as diet, lifestyle, and/or medications can also alter the patient's condition on both short term and long term basis. Thus, at least certain patients are scheduled for follow up clinical visits wherein a clinician reevaluates the patient's condition and may adjust the operating parameters of the device via telemetric interrogation with assistance of a physician's programmer.

Thus, it will be appreciated that there is a need in at least certain applications for ongoing monitoring and possible reprogramming of an implantable therapeutic device throughout an implantation period. There exists a similar need to reduce time burdens and inconvenience on the clinician and the treated patient to perform these follow up evaluations and possible readjustments. It would also be advantageous to provide the ability to more timely adjust operating programming of an implantable device closer in time to changes in the patient's condition indicating such readjustment rather than waiting for a follow up clinical visit.

SUMMARY

What are described herein are systems and methods for individually adapting operational parameters of an implantable therapy device for improved performance for an individual patient throughout an implantation period. In certain aspects, electrogram data can be gathered to evaluate the electrical activity of the patient's heart and impedance data can be gathered to evaluate mechanical activity of the patient's heart. Transcardiac impedance measurements provide signals indicative of the amount of blood within the heart, e.g. blood inflow and outflow as well as signals indicative of myocardial thickening/thinning. These signals can be evaluated as indicators of the electromechanical activity of the heart and can be utilized to determine adjustments needed, for example for improved chamber to chamber synchrony and/or overall cardiac performance.

In certain implementations, this can include determining and comparing delay times between initiation of depolarization as indicated by an intracardiac electrogram (IEGM) and peak myocardial contractility as indicated by a peak in a transcardiac impedance measurement. Measurements can be performed along multiple spatially arranged sensing vectors to determine data indicative of the activity of specific regions of the patient's heart.

In order to better understand relationships between internally sensed parameters, for example IEGMs and impedance measurements, in certain embodiments, external sensing can be employed to provide alternative measures of the patient's activity. For example, ultrasonic imaging can be employed in certain implementations to perform tissue Doppler echocardiography and strain/strain rate measurements. Sonographic imaging can also provide direct measures of cardiac performance, such as ejection fractions (EF).

Certain embodiments include determining a base line or template corresponding generally to desired physiologic performance. For example, in certain implementations a number of patients exhibiting desired physiologic performance can be evaluated to derive an ensemble average of characteristics indicating normal healthy activity. This can be referred to as eucontractile behavior. It will be understood as used herein that eucontractile or desired physiologic performance does not necessarily indicate that the source of the data is in all respects healthy and normal but simply that the characteristics of interest are substantially the same as an otherwise healthy patient.

In certain implementations, these templates can be determined both at rest state and at an elevated metabolic state, for example as determined during exercise or Dobutamine infusion. These implementations can thus provide a rate responsive range of baseline data such that appropriate adjustments can be determined over a range of patient metabolic rates. By comparing data indicative of the patient's current physiologic performance with the desired baseline or template data, any indicated adjustments can be determined on an ongoing manner. For example, in one implementation, adjustments can be made at the time of implantation to provide an improved initial set of operating parameters. Subsequently as the patient tissue accommodates the newly implanted device and leads, their performance can be reevaluated and adjusted as indicated to accommodate for any changes in the device tissue interface.

Certain implementations also provide the ability for the implantable device itself to independently periodically evaluate sensed indications of the patient's physiologic performance and compare these indications to the desired baseline and make any indicated adjustments. Thus, in certain implementations, the implantable device is adapted for closed loop self programming such that the device can improve its performance without direct intervention of an attending clinician. This ability facilitates more timely adaptation to changes in the patient's condition, for example due to stress, medication, elevated metabolic rate, etc.

One embodiment includes an implantable cardiac stimulation device comprising an implantable stimulation pulse generator adapted to generate therapeutic stimulation, at least one implantable lead defining at least one stimulation circuit and one sensing circuit adapted to sense at least one physiologic parameter indicative of a patient's physiological activity and a controller in communication with the at least one lead so as to receive signals indicative of the patient's physiologic activity and with the stimulation pulse generator such that the controller can selectively induce delivery of the therapeutic stimulation and wherein the controller operates under a first programmed set of a plurality of variable operational parameters wherein the operational parameters define timing intervals under which the therapy is delivered and characteristics of the therapy delivered, and wherein the controller is further adapted to periodically evaluate signals indicative of the patient's cardiac activity for effectiveness of the therapy delivery and wherein the controller is further adapted to automatically self-reprogram the first set of operational parameters to a second set of operational parameters to improve effectiveness of the timing intervals of the therapy delivery.

Another embodiment includes a method of delivering therapy by an implantable stimulation device, the method comprising programming an implantable device with a first set of a plurality of operational parameters that define characteristics, including timing characteristics, of therapy to be delivered and conditions under which the therapy is delivered, designating at least one indicator of cardiac performance, monitoring a patient's physiologic activity by the implantable device, evaluating the patient's physiologic activity by the implantable device, generating and delivering therapeutic stimulation by the implantable device as a function of the monitored physiologic activity, at least periodically evaluating the at least one indicator of cardiac performance by the implantable device under therapy provided according to the first set of operational parameters, and reprogramming the first set of operational parameters to a second set of the operational parameters by the implantable device upon indications that delivery of the therapeutic stimulation can be improved.

Yet another embodiment includes a therapeutic device system comprising an implantable therapeutic stimulation device comprising an implantable stimulation pulse generator adapted to generate therapeutic stimulation, at least one implantable lead defining at least one stimulation circuit and one sensing circuit adapted to sense at least one physiologic parameter indicative of a patient's physiological activity, and a controller in communication with the at least one lead so as to receive signals indicative of the patient's cardiac activity and with the stimulation pulse generator such that the controller can selectively induce delivery of therapeutic stimulation under a set of a plurality of operational parameters that define interval timing characteristics and parameters for delivery of the therapy, an external user interface adapted to display data and convert user inputs into control signals, and telemetry adapted for communication between the implantable stimulation device and the external user interface such that the external user interface can program an initial set of the operational parameters and wherein the controller is adapted to evaluate the patient's cardiac activity and autonomously closed-loop reprogram at least the interval timing parameters to improve delivery of the therapeutic stimulation for improved electromechanical synchrony. These and other objects and advantages of the invention will become more apparent from the following description taken in conjunction with the accompanying drawings.

BRIEF DESCRIPTION OF THE DRAWINGS

FIG. 6 illustrates schematically two wave forms indicative of a patient's right ventricular and left ventricular activity and illustrating differences in synchronization there between.

DETAILED DESCRIPTION

Reference will now be made to the drawings wherein like numerals refer to like parts throughout. The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
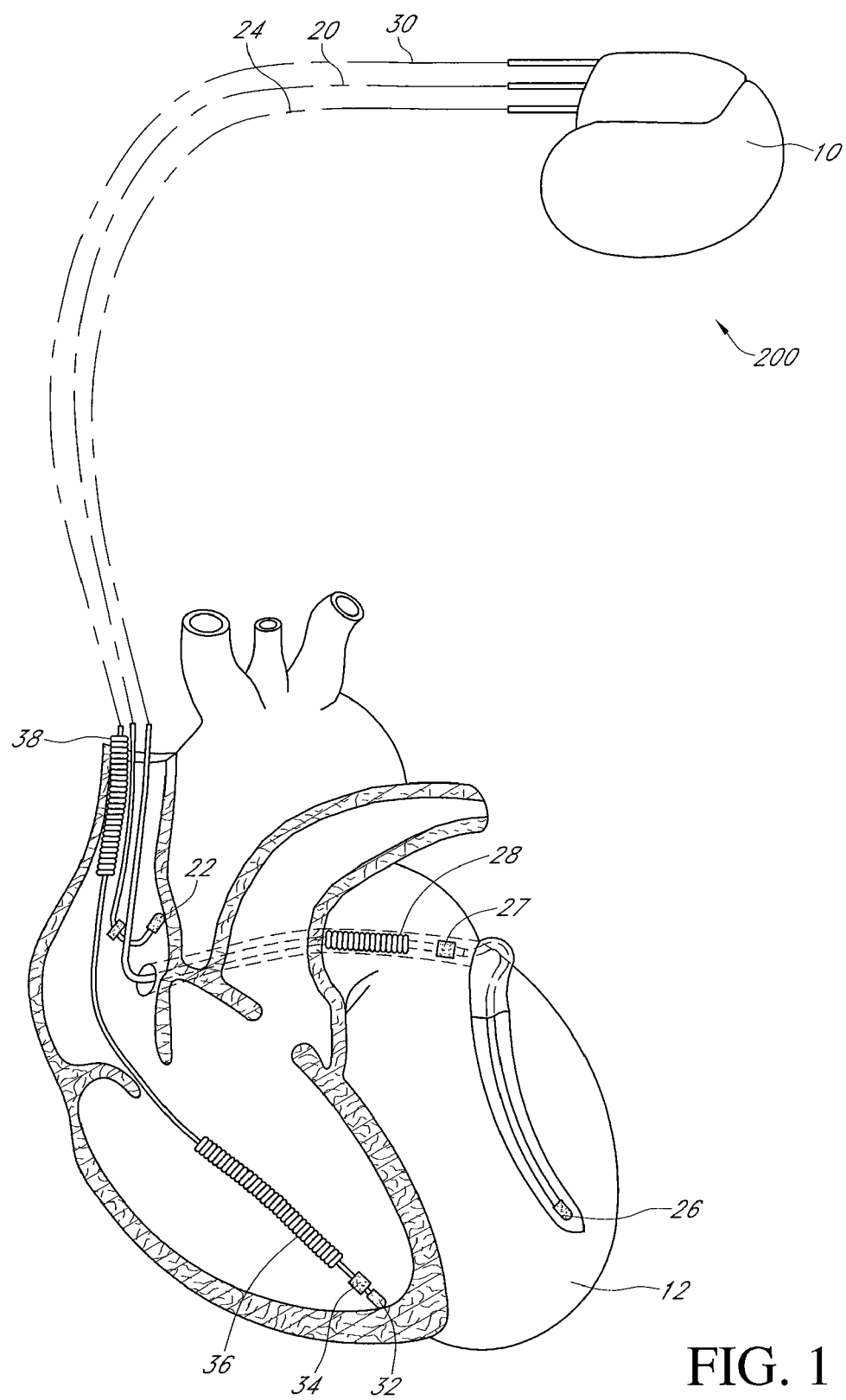
FIG. 1 is a simplified diagram illustrating a therapeutic appliance with an implantable stimulation device in electrical communication with at least three leads implanted into a patient's heart for delivering multi-chamber stimulation and shock therapy.

In one embodiment of a therapy system 200, as shown in FIG. 1, a device 10 comprising an implantable cardiac stimulation device 10 is in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
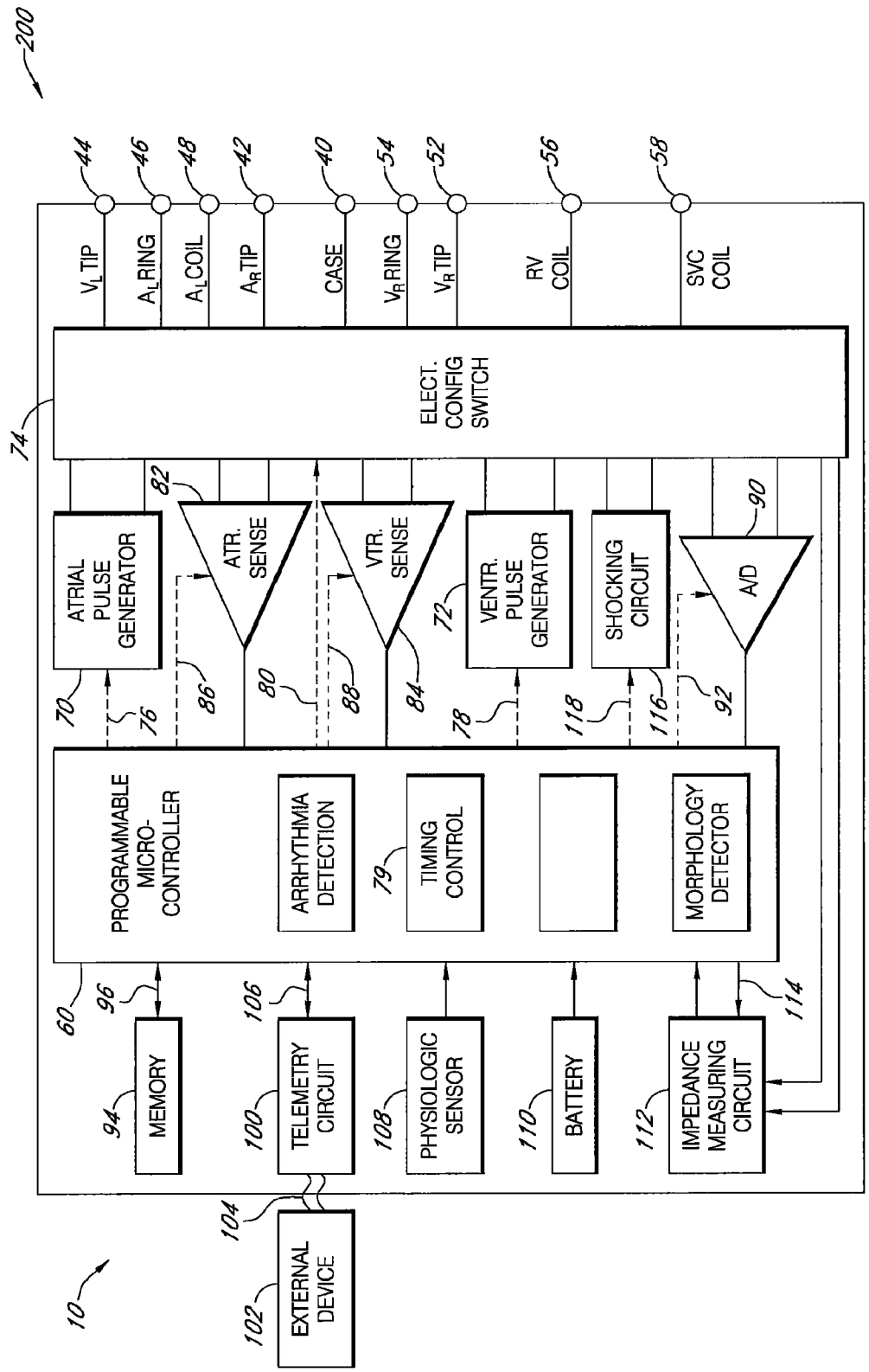
FIG. 2 is a functional block diagram of a multi-chamber implantable stimulation device illustrating elements of a stimulation device that can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all pacemaker "unipolar" modes. The housing 40 may further be used as a return electrode alone or in combination with one or more of the coil electrodes, 28, 36 and 38, for shocking purposes. The housing 40 further includes a connector having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions is well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. In this embodiment, the switch 74 also supports simultaneous high-resolution impedance measurements, such as between the case or housing 40, the right atrial electrode 22, and right ventricular electrodes 32, 34 as described in greater detail below.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independently of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, timing/delays and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows IEGMs and status information relating to the operation of the device 10 (as contained in the microcontroller 60 or memory 94) to be sent to the external device 102 through an established communication link 104.

In certain preferred embodiments, the stimulation device 10 further includes a physiologic sensor 108, commonly referred to as a "rate-responsive" sensor because it can be used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 that provides operating power to all of the circuits shown in FIG. 2. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, embodiments of the device 10 including shocking capability preferably employ lithium/silver vanadium oxide batteries. For embodiments of the device 10 not including shocking capability, the battery 110 will preferably be lithium iodide or carbon monoflouride or a hybrid of the two.

As further shown in FIG. 2, the device 10 is shown as having an impedance measuring circuit 112 that is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
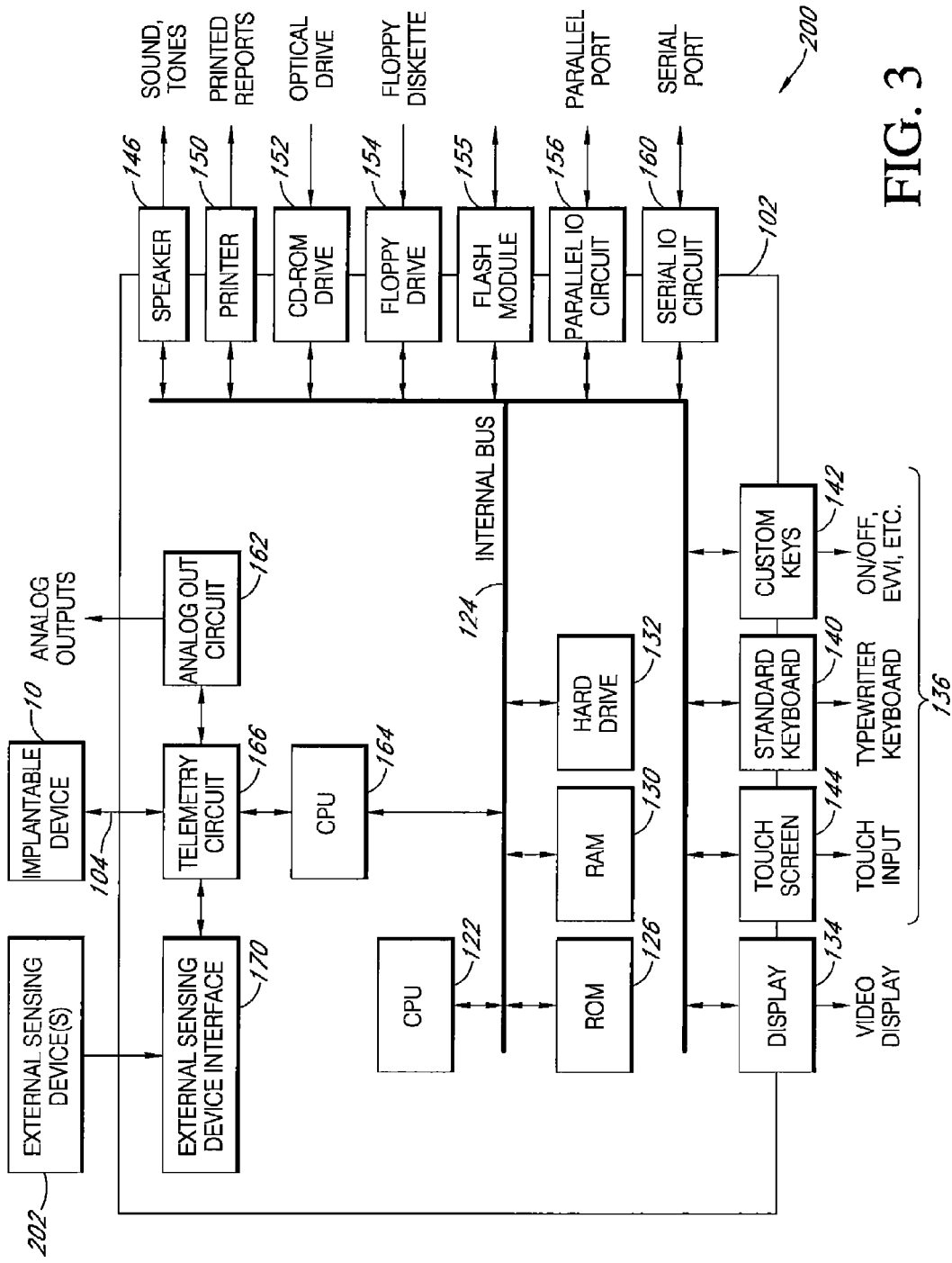
FIG. 3 is a functional block diagram of one embodiment of a physician's programmer capable of establishing communication with an implantable medical device and with one or more external sensing devices.

FIG. 3 is a functional block diagram of one embodiment of an external device 102, such as a physician's programmer. The external device 102 is adapted to provide connectivity with the implantable device 10 and with one or more external sensing devices 202. The external device 102 is further adapted to display data indicative of signals received from the implantable device 10 and the external sensing device(s) 202. The external device 102 is also adapted to send commands to the implantable device 10, for example to adjust the programming of the device 10.

In one embodiment, the external device 102 comprises a CPU 122 in communication with an internal bus 124. The internal bus 124 provides a common communication link and power supply between various electrical components of the external device 102, for example including the CPU 122. The external device 102 also comprises memory and data storage that can include one or more of ROM 126, RAM 130, and a hard drive 132 in communication with the internal bus 124. The ROM 126, RAM 130, and hard drive 132 provide temporary memory and non-volatile storage of data in a well-known manner. In one embodiment, the ROM 126, RAM 130, and/or hard drive 132 can store control programs and commands for upload to the implantable device 10 as well as operating software for display of data received from the implantable device 10 and/or from one or more external sensing devices 202. It will be appreciated that in certain embodiments alternative data storage/memory devices, such as flash memory, can be included or replace one or more of the ROM 126, RAM 130, and hard drive 132 without detracting from the spirit of the invention.

The external device 102 also comprises a display 134. The display 134 is adapted to visually present graphical and alphanumeric data in a manner well understood in the art. For example, in certain embodiments, the display 134 and the external device 102 are adapted to display waveforms indicative of a patient's physiologic activity based at least partially on signals received from the implantable device 10 and/or the one or more external sensing devices 202. In various implementations, the external device 102 is adapted to display one-dimensional curvilinear waveforms and/or two-dimensional images indicative of the patient's physiologic activity. The display 134 is also adapted to display status information for the implantable device 10, such as current programming settings.

The external device 102 also comprises one or more input devices 136 to enable a user to provide commands and input data to the external device 102. In one embodiment, the input devices 136 include a keyboard 140, a plurality of custom keys 142, and a touch screen 144 aspect of the display 134. The keyboard 140 facilitates entry of alphanumeric data into the external device 102. The custom keys 142 can be programmable to provide one touch functionality of predefined functions and/or operations. The custom keys 142 may be embodied as dedicated touch keys, such as associated with the keyboard 140 and/or predefined areas of the touch screen 144. In this embodiment, the external device 102 also comprises a speaker 146 and a printer 150 in communication with the internal bus 124. The speaker 146 is adapted to provide audible signals to a user. The printer 150 is adapted to provide a printed readout of information from the external device 102.

In one embodiment, the external device also comprises one or more of an optical drive 152, a floppy drive 154 and flash module 155 which together provide removable data storage. In this embodiment, the external device also includes one or more of a parallel input-output (IO) circuit 156, a serial 10 circuit 160, and an analog output circuit 162. These circuits 156, 160, 162 provide a variety of communication capabilities between the external device 102 and other devices in a manner well understood in the art.

The external device 102 also comprises an external sensing device interface 170 adapted for communication with the one or more external sensing devices 202. In certain embodiments, the external sensing device interface 170 is adapted for wired communication with the one or more external sensing devices 202. In certain embodiments, the external sensing device interface 170 is adapted for wireless communication with the one or more external sensing devices 202. The external sensing device interface 170 can include amplifiers, A/D-D/A converters, bandpass filters, and/or overcurrent/overvoltage protection circuits depending on the requirements of specific applications.

The external sensing devices 202 provide data indicative of a patient's condition obtained from at least partially externally arranged sensing. It will be understood that in certain implementations, the external sensing devices 202 are adapted to sense patient physiologic activity that at least partially occurs within the patient's body. As used herein, external sensing refers to sensing, for example with one or more embodiments of the external sensing devices 202, wherein at least certain physical sensing components are arranged externally of the patient, for example on a skin surface. In certain embodiments, the external sensing devices 202 can employ radiated or transmitted energy, such as sonic energy and/or electromagnetic energy that propagates internally within the patient.

In one embodiment, the external sensing device 202 comprises a surface ECG sensor 202. The surface ECG sensor 202 includes a plurality of ECG leads that are adapted for placement on the patient's skin. The ECG sensor 202 obtains electrical signals from the surface of a patient's body and configures the signals for display as an ECG waveform on the display 134 of the external device 102.

In another embodiment, the external sensing devices 202 comprise an external impedance sensor 202. In this embodiment, the external impedance sensor 202 obtains electrical impedance measurements indicative of the time varying impedance of patient tissue and fluids/solids interposed between sensing electrodes. In certain embodiments, sensing electrodes of the external impedance sensor 202 are preferably arranged to define multiple spatial vectors such that impedance measurements can be obtained along multiple spatially arranged paths.

In a further embodiment, the external sensing devices 202 comprise an ultrasonic imager 202. The ultrasonic imager 202 is adapted to deliver sonic energy to the patient's body and sense at least one of reflected and transmitted sonic energy. The ultrasonic imager 202 can thus develop signals indicative of the internal structure and activity of the patient. In certain embodiments, the ultrasonic imager 202 is further adapted to perform continuous wave and/or pulsed Doppler measurements such that the ultrasonic imager 202 can also develop signals indicative of velocity characteristics of selected patient tissue/fluids. Impedance measurements and ultrasonic imaging can provide data indicative of mechanical properties of the patient as will be described in greater detail below.

The external device 102 also comprises telemetry CPU 163 and a telemetry circuit 166 that can establish the telemetric link 104 in cooperation with the implantable device 10 and optionally with one or more of the external sensing device(s) 202. The telemetric link 104 comprises a bidirectional link to enable the external device 102 and the implantable device 10, for example, to exchange data and/or commands. The establishment of the telemetric link 104 is, in certain embodiments, facilitated by a wand or programmer head that is placed in proximity to the implantable device 10. The wand or programmer head facilitates establishment of the telemetric link 104 by placing an antenna structure in a closer proximity to the implantable device 10 to facilitate conduction of transmitted signals to the external device 102.

The telemetric link 104 can comprise a variety of communication protocols appropriate to the needs and limitations of a given application. In certain embodiments, the telemetric link 104 comprises radio frequency (RF) telemetry. In one particular embodiment, the telemetric link 104 comprises a frequency modulated digital communication scheme wherein logic ones are transmitted at a first frequency A and logic zeros are transmitted at a second frequency B. As previously noted, the implantable device 10 is powered by a battery having limited capacity. In certain embodiments, the external device 102 is powered by line voltage, e.g., is not subject to the stringent power limitations of the implantable device 10. Thus, in certain embodiments, the bidirectional telemetric link 104 can proceed in an asymmetric manner.

For example, in one embodiment, a transmission power and data rate from the external device 102 to the implantable device 10 via the telemetric link 104 can proceed at higher power levels and/or higher data transmission rates than the reciprocal data rates and transmission power from the implantable device 10 to the external device 102. The telemetry circuit 100 of the implantable device 10 as well as the telemetry circuit 166 and CPU 164 of the external device 102 can select or be adjusted to provide a desired communication protocol and transmission power in a manner which will be well understood by one of ordinary skill.

The therapy system 200 is configured to measure and evaluate a patient's physiology and further adapted to adjust therapy delivery in an individualized manner to optimize the therapy for the needs and condition of the individual patient. As used herein, the terms "optimal", "optimize," "optimizing," "optimization", "minimize", "maximize" and the like are to be understood as commonly used terms of the art referring simply to a process of evaluating and adjusting or individualizing the operating parameters of a system for improved performance in an individual application. It will be understood that the physiologic activity and characteristics of an individual, for example their cardiac activity, is subject to both random variations, cyclical variations, diurnal variations, and long-term variations. An individual patient's physiologic activity is also subject to variation brought about by medication dosing. Environmental factors and noise are generally asynchronous and unpredictable by an automated therapy system and can, at least in certain implementations, impair complete isolation of signals of interest.

Thus, the matching of therapy systems and methods to precise instantaneous needs of a patient is, as a practical matter, an inexact science. Thus, use of the terms "optimal", "optimize," "optimizing," "optimization" and the like does not imply that the described process results in a perfect setting for a system or method as used with an individual patient or that any further improvements are not available. Thus, the terms "optimize," "optimizing," and/or "optimization" are to be interpreted as relative terms indicating generally improved performance in an individual application and are not to be interpreted as absolutes.

Figure 4:
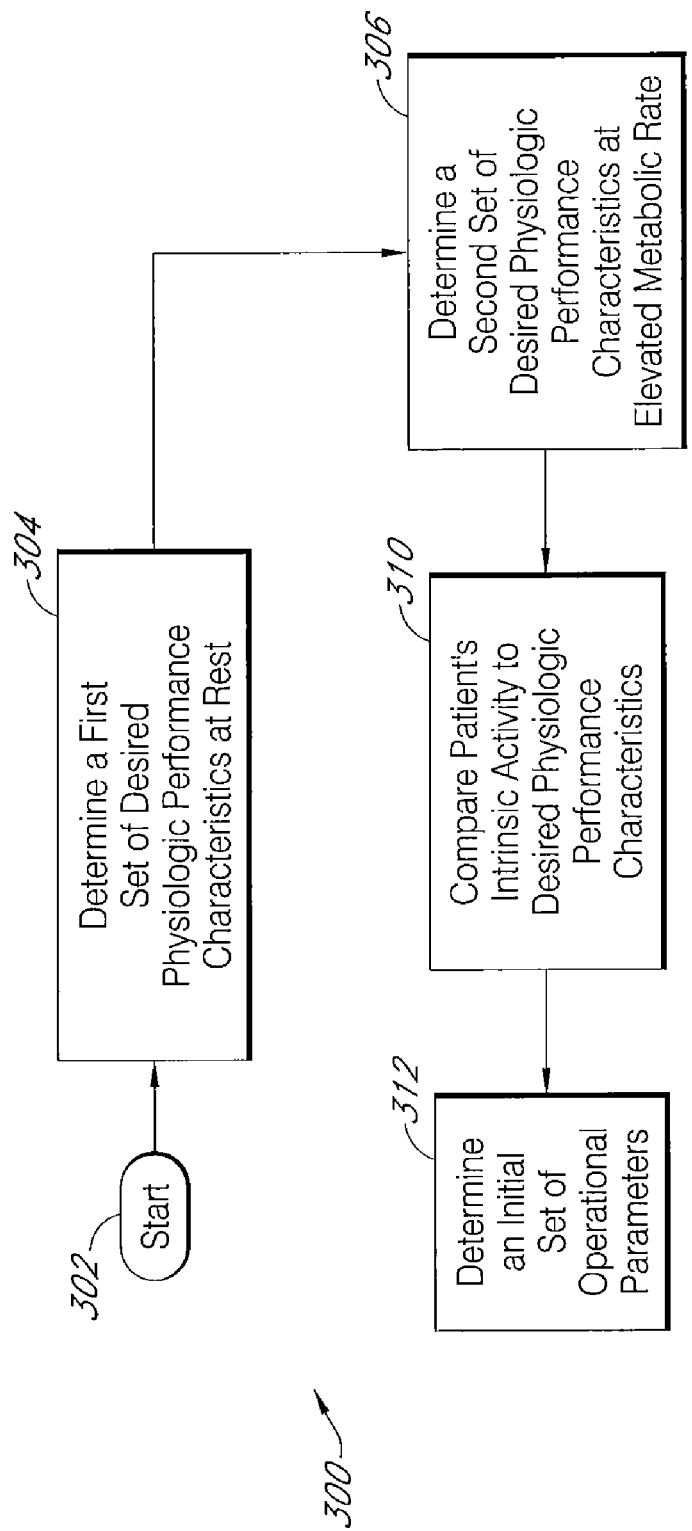
FIG. 4 illustrates one embodiment of a method of operating an implantable therapy device for improved individual adaptation of the device.

FIG. 4 illustrates one embodiment of a method 300 of operating the therapy system 200 for improve individual adaptation of therapy delivery for a particular patient's needs. Following from a start block 302, a block 304 includes determination of a first set of desired physiologic performance characteristics at rest. In one implementation, the block 304 includes analyzing or evaluation one or more eucontractile patients having similar physiology to the implantable device patient. As previously noted, eucontractile does not necessarily indicate that the subject is fully healthy and normal, but simply that they display generally the desired physiologic performance of interest. In certain implementations, the determination of block 304 can include statistical methods, including ensemble averaging of a plurality of eucontractile patients having similar physiology to the implantable device patient. Additional details of systems and methods for determining desired physiologic performance characteristics can be found in the co-owned application A05E4002 that is incorporated herein by reference in its entirety.

In a block 306, a second set of desired physiologic performance characteristics is determined at elevated metabolic rates. In certain implementations, the second set of characteristics of block 306 can be determined during controlled exercise in a clinical setting. However, due to technical difficulties in obtaining accurate measures under conditions of patient movement, in certain implementations it will be preferred that the determination of block 306 be performed under Dobutamine. The determination of blocks 304 and 306 provide multiple data sets of representative physical characteristics such that desired performance can be determined throughout the typical range of patient metabolism.

Following in a block 310, the patient's intrinsic activity is obtained and compared to the determined desired characteristics from block 304 and 306. As in at least certain implementations, the system 200 and method 300 are adapted to facilitate closed loop or self-programming by the device 10, in these implementations it will be preferred that blocks 304, 306, and 310 be at least partially based on internally sensed data. Thus, in certain implementations, the first and second sets of desired physiologic performance characteristics are obtained from eucontractile patients with a sensing configuration similar to that which will be provided to the implantable device patient. In certain implementations, it will be preferred that the desired baseline or template data be obtained with sensing and stimulation electrodes of the device 10 arranged substantially similar to what will be implemented for the implantable device patient.

Following from the comparison of block 310, in a block 312 an initial set of operation parameters are determined. While a large number of individual operational parameters can exist and the particular nature and combination of these parameters will be dependent upon the individual patients need and configuration of the device 10, generally such operating parameters include stimulation amplitude, refractory periods, inter and intrachamber delays, detection thresholds, gain settings, and the like as will be well understood of one of ordinary skill.

In certain implementations, preferred locations for ventricular electrodes are adjacent the RV septum (Basal or High Septum) and the lateral LV wall via a bipolar CS lead. These locations provide data which is more congruent with data acquired ultrasonically, such as via the external measurement system 202. In other implementations, a preferred placement for RV leads is in the RV septal location. In other implementations, an electrode is preferably engaged with the septum with the RV coil electrode arranged in the RV apex. In yet other embodiments, RV apical leads can be used but will generally be less preferred.

Figure 5:
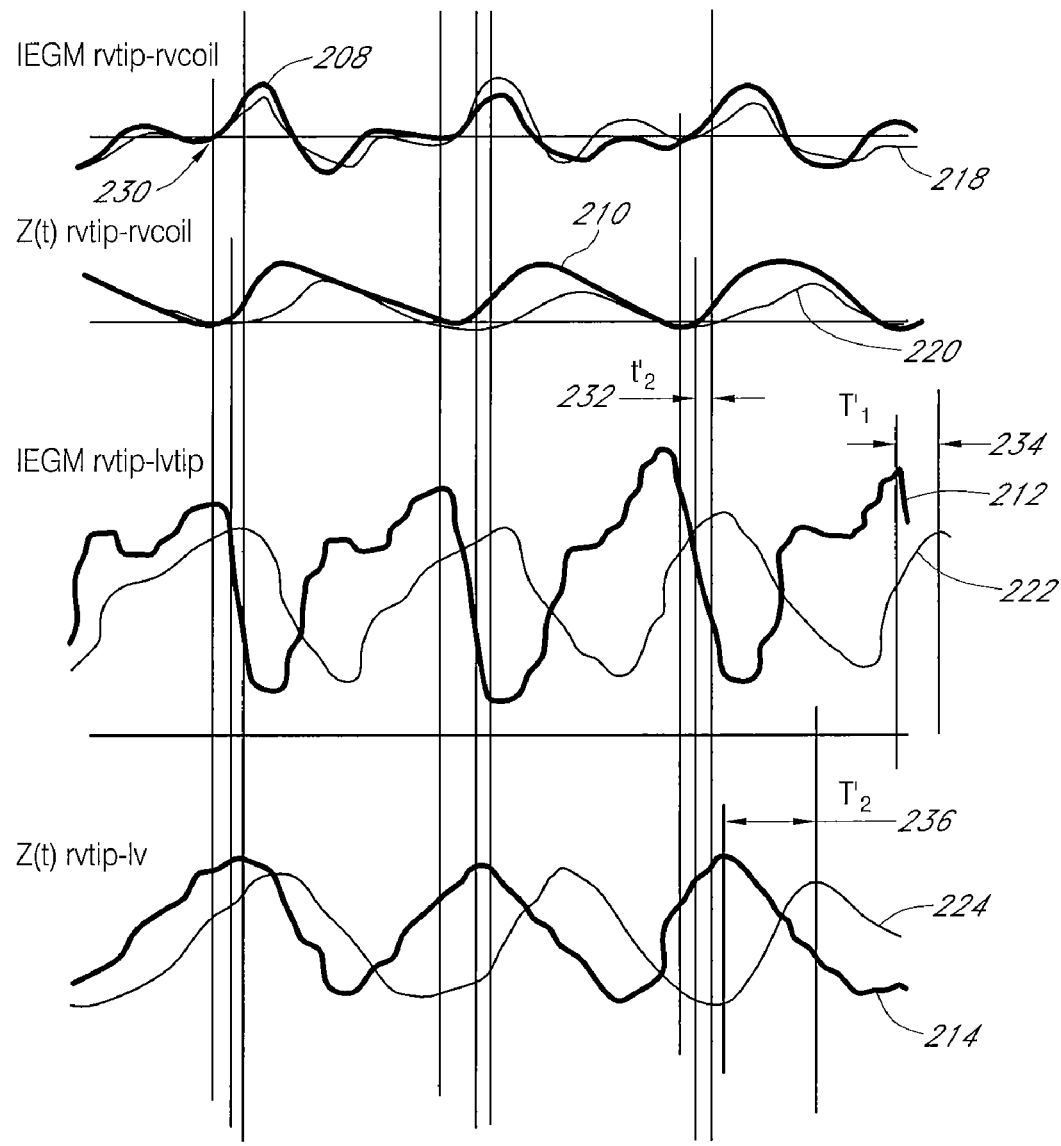
FIG. 5 illustrates an overlay of exemplary waveforms of a representative eucontractile patient and a dysfunctional patient with one embodiment of determining correction factors.

FIG. 5 illustrates exemplary waveforms indicating desired physiologic performance and an implantable device patient's actual physiologic performance. FIG. 5 illustrates a desired IEGM waveform 208 as measured between an RV tip electrode and an RV coil electrode. The corresponding patient's activity is indicated by the curve 218. Similarly, FIG. 5 illustrates a desired time varying impedance curve 210 as measured between an RV tip and an RV coil electrode and a corresponding patient's curve 220.

FIG. 5 also illustrates a eucontractile waveform 212 of an IEGM sensed between an RV tip and an LV tip electrode. The corresponding patient's activity is indicated by the curve 222. Similarly, FIG. 5 illustrates a desired template time varying impedance curve 214 as measured between an RV tip and an LV electrode and corresponding patient's curve 224.

FIG. 5 also illustrate, for example, A-V delays within a single cardiac cycle as well as A-A and V-V delays across consecutive cardiac cycles as indicated by the IEGM signals. As previously noted, the device 10 is capable of varying these as well as other delays. Various embodiments provide the ability to optimize these as well as other operational parameters of the device 10, for example in a rate responsive manner.

As previously noted, the eucontractile data illustrated in FIG. 5 is in certain embodiments based upon measurements made of a plurality of patients having similar cardiac geometries/dimensions. Thus, the activity illustrated in FIG. 5 may not correspond precisely to any given individual patient, but is rather illustrative generally of a desired normal eucontractile characteristic. It will also be understood that the waveforms of FIG. 5 are only for illustrative purposes and should not be interpreted as being accurately to scale or morphology.

FIG. 5 also illustrates that this embodiment also includes the calculation of temporal correction factors. In this embodiment, an examination or evaluation is made between the dysfunctional patient's electro-mechanical cardiac activity as compared to an otherwise comparable eucontractile patient's. In one embodiment, the electrical characteristics of the dysfunctional patient are compared to those of a corresponding eucontractile patient for possible indications of a stimulation deficit.

A first temporal correction factor $t'_1$ 230 would indicate a stimulation deficit and be exhibited by a temporal mismatch between the curves 208 and 218. In this embodiment, while the dysfunctional and the eucontractile patients exhibit magnitude differences in the respective IEGM RV tip to RV coil waveforms 208, 218, the waveforms are substantially temporally synchronized and in this embodiment a first temporal correction factor $t'_1$ is effectively null. Thus, in this embodiment, this particular dysfunctional patient is not exhibiting a stimulation deficit in the RV tip to RV coil dimension and modification of their therapy in this aspect would not be indicated.

In this embodiment, the patient does exhibit a degree of stimulation deficit along the IEGM RV tip to LV tip dimension. More particularly, it can be seen that a difference exists in the temporal dimension between the IEGM curves 210, 220 for the eucontractile and dysfunctional patients, respectively. Thus, in this embodiment, a second temporal correction factor $t'_2$ 232 would be indicated. The second temporal correction $t'_2$ 232 indicates a time by which therapeutic stimulation should be pre-excited in its delivery to the patient to compensate for the temporal mismatch in the dysfunctional patient's electrical cardiac activity along the RV tip to LV tip dimension.

Similarly, temporal correction factors can be evaluated for the patient's mechanical activity for indication of contraction deficits. In this embodiment, a third temporal correction factor $T'_1$ would be indicated for the patient as indicated by the reference designator 234 of FIG. 5. The third temporal correction factor $T'_1$ corresponds to a delay or mismatch in the dysfunctional patient's impedance measurement Z(t) along the RV tip to RV coil dimension. A fourth temporal correction factor $T'_2$ 236 would also be indicated in this embodiment due to the delay or mismatch of the dysfunctional patient's impedance curve Z(t) RV tip to LV 224 as compared to the eucontractile impedance curve Z(t) RV tip to LV 214. The third and fourth temporal correction factors $T'_1$ and $T'_2$ 234, 236 correspond to contraction deficits in the dysfunctional patient along the RV tip to RV coil and RV tip to LV vectors, respectively.

In this embodiment, any indicated temporal correction factors, for example, for stimulation deficits and/or contraction deficits along a given dimension or vector are summed to obtain a total electro-mechanical temporal correction factor indicated for delivery of therapy along that vector. For example, in one embodiment, the first temporal correction factor $t'_1$ is effectively null corresponding to the lack of contraction deficits in this patient along this vector and the total temporal correction factor would correspond simply to the third temporal correction factor $T'_1$ corresponding to the dysfunctional patient's contraction deficit along the RV tip to RV coil dimension. Similarly, the total electro-mechanical temporal correction factor needed along the RV tip to LV dimension would equal $t'_2$ plus $T'_2$ to account for both the stimulation deficit and contraction deficit along the RV tip to RV vector. The total electro-mechanical temporal correction factors are used to adjust the delivery of therapeutic stimulation to attempt to restore the dysfunctional patient's cardiac activity to closer conformance with the electro-mechanical cardiac activity of a comparable eucontractile patient.

Again, in certain embodiments, any indicated temporal correction factors are used to determine a pre-excitation period or delay to adjust the timing of delivery of therapeutic stimulations. In certain embodiments, the temporal correction factors are determined over a range of metabolic rates. It will be understood that in certain applications the indicated temporal correction factors will vary as a function of rate. In certain implementations, a given correction factor can be null for some rates and present at other rates.

Determination of appropriate stimulation strengths, for example voltage and current to be delivered can also be determined through analysis of evoked potentials as currently employed in known pacing systems. Alternatively, or in addition, determination of appropriate therapeutic stimulation intensity is based in certain embodiments on measurements of threshold data obtained during evaluation of device function, for example, via capture threshold measurements.

Figure 6:
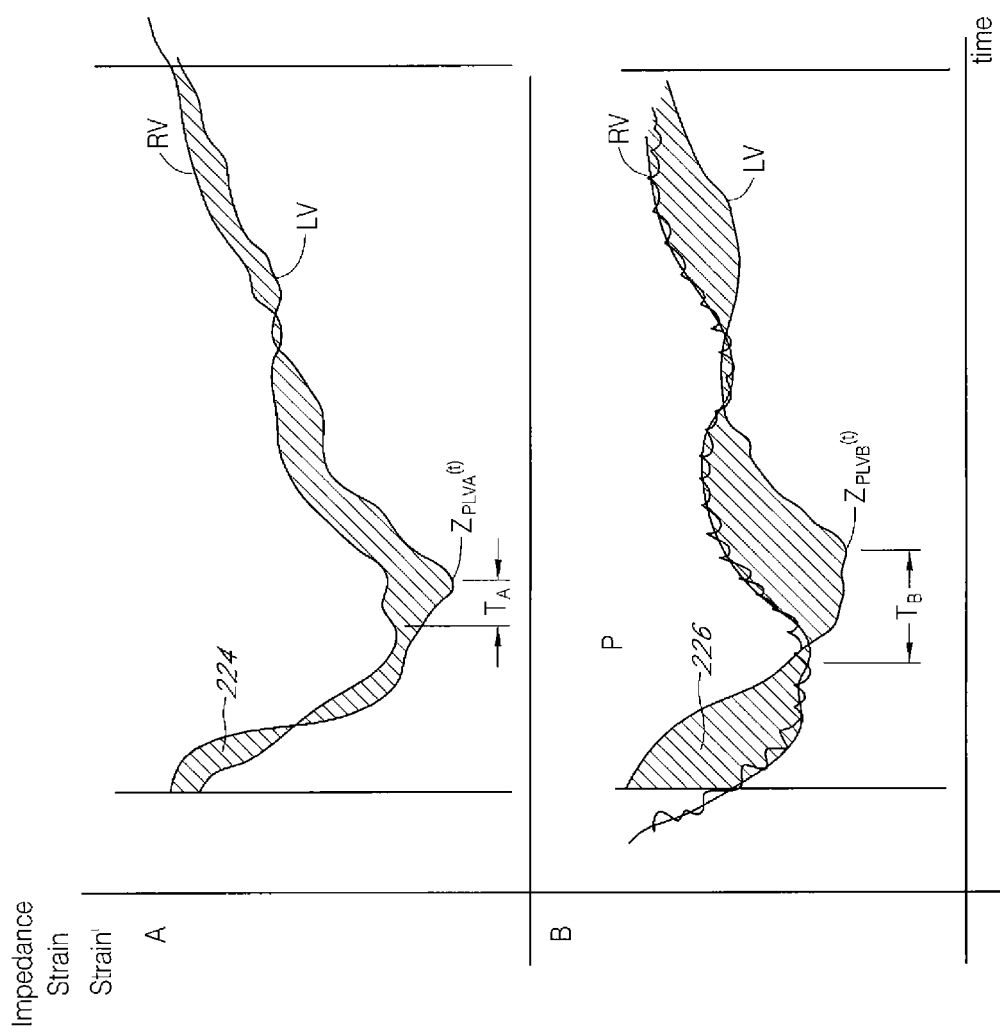

FIG. 6 illustrates another methodology that can be used to characterize a patient's synchrony characteristics. In this embodiment, myocardial impedance curves are obtained from regions of interest, for example in the septum, lateral wall or other myocardial regions to develop curves indicating the activity of the RV and LV. In certain embodiments, strain, strain rate, and/or velocity measurements can also be made, for example via the external sensing devices 202. Differences between the RV and LV curves can be integrated over time to obtain an effective area between the curves or difference integrals indicative of the relative synchrony/dysynchrony between the RV and LV.

FIG. 6 illustrates first and second sets of curves A and B and corresponding first and second difference integrals 224, 226 corresponding to the areas of the shaded regions bounded by the RV and LV curves. A comparison will reveal that the first difference integral 224 is less than the second difference integral 226 indicating a higher degree of synchrony for the RV and LV curves A than for curves B. Thus, the difference integral 224 corresponds to improved performance as compared to difference integral 226.

FIG. 6 also illustrates a time interval $T_A$ between peak RV and LV contractility and a corresponding $T_B$ for the curve B. Similarly, to the difference integrals 224, 226, the time interval $T_A$ is less than the interval $T_B$ indicating improved synchrony. Again, optimal performance does not imply that further improvements are not possible, but the curve A represents optimized performance as compared to that indicated by the curve B.

FIG. 6 also illustrates that in one embodiment peak impedance amplitudes can be identified and compared as relative indicators of the patient's cardiac performance. In this embodiment, as a patient's overall cardiac performance is highly related to their left ventricular output, the peaks of left ventricular impedance are identified. The time varying impedance signal peaks comprise local minima corresponding to an increased amount of blood interposed between the sensors generating the impedance signal as well as a reduction in the impedance component corresponding to the interposed myocardium. The impedance signal peaks also comprise local maxima corresponding to decreased amounts of blood interposed between the sensors generating the impedance signal as well as increased impedance components corresponding to the interposed myocardium. Thus, the "peaks" of the impedance signal can comprise local minima and/or local maxima.

As illustrated in FIG. 6, the minima peak amplitude of left ventricular activity for curve A $Z_{PLVA}(t)$ exhibits a greater excursion than the corresponding minima peak for the curve B $Z_{PLVB}(t)$. In general, higher amplitude local maxima peaks and lower magnitude local minima peaks indicate more optimal performance. The larger excursion peaks are associated with more complete ejection of blood and contraction of cardiac tissue and similarly more complete refilling of blood in the heart 12 and relaxation of the cardiac tissue.

Thus, in certain embodiments, adjustments can be made in the operational parameters of the device 10 to improve direct measures of cardiac performance, for example peak impedance measurements, without requiring comparison to desired baseline templates. For example, the device 10 can be configured to increase the amplitude excursions of the impedance peaks or similarly to increase peak-to-peak differences between local maxima and minima. As the device 10 can be configured to perform impedance measurements independently, certain embodiments support the capability for the device 10 to perform closed loop or self-programming to improve the performance of the device 10 without requiring the direct intervention of a clinician to adjust the device's programming.

Figure 7:
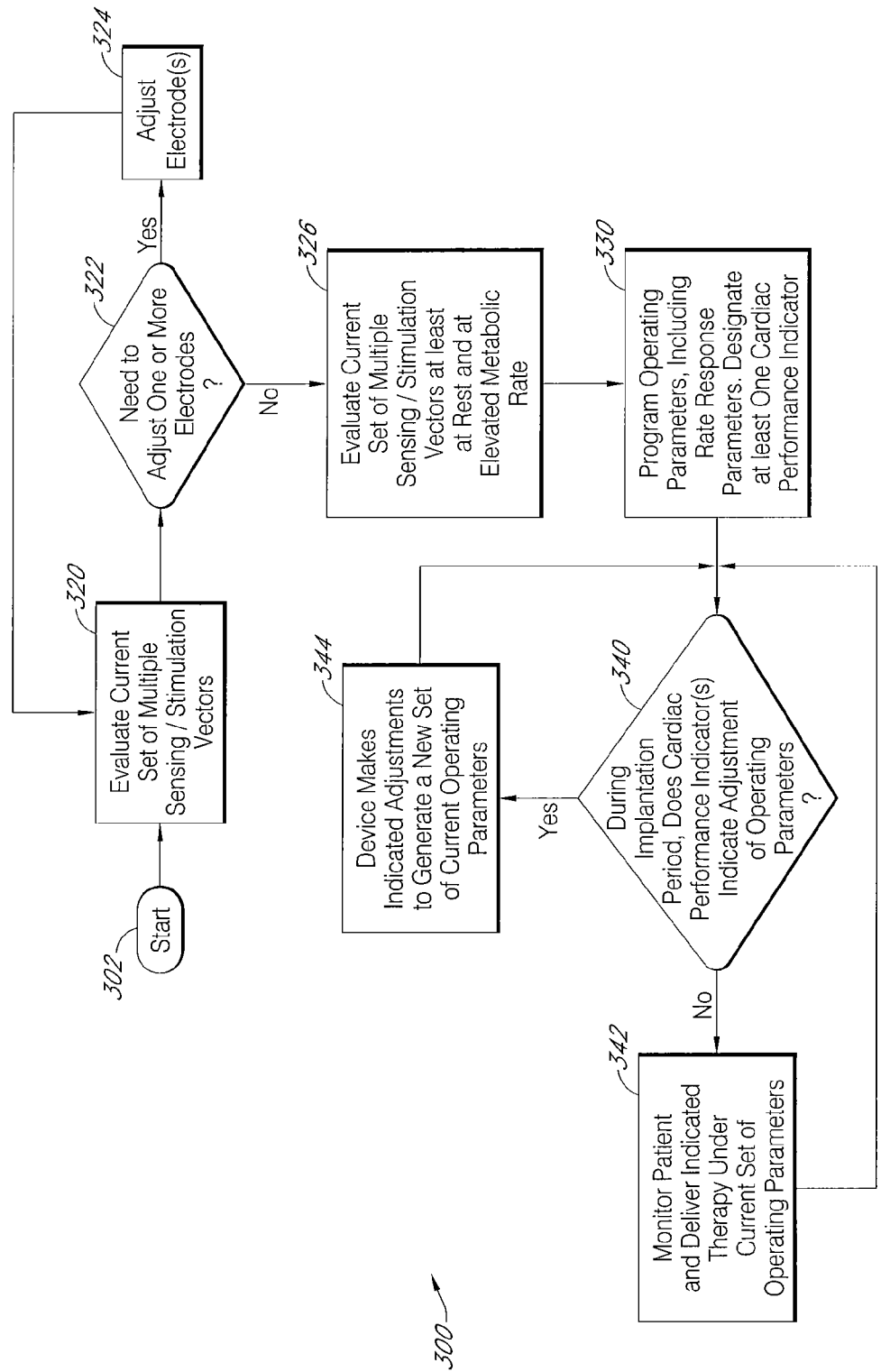
FIG. 7 illustrates another embodiment of a method of operating an implantable therapy device for improved individual adaptation of the device.

FIG. 7 illustrates additional aspects of one embodiment of a method 300 of employing a therapeutic system 200 for improved optimization or individual adaptation of an implantable therapeutic device 10 for the needs and circumstances of an individual patient. Following from a start block 302, in a block 320 a current set of multiple sensing/stimulation vectors are evaluated with respect to the physiologic performance of the patient. In certain embodiments, block 320 can comprise one or more of the blocks 304, 306, 310, 312 as previously described with respect to FIG. 4. However, in certain embodiments, the method 300 need not include the blocks 304, 306, 310, 312. Thus, the method 300 need not necessarily include determination and comparison to a reference template but can simply proceed based on evaluation of the individual patient's performance.

As previously noted, the device 10 is preferably configured to support sensing and delivery of stimulation to multiple locations of the patient's heart 12 which thus define multiple spatially arranged sensing and stimulation vectors. This aspect provides increased flexibility in adjusting or optimizing sensing of the patient's physiologic activity as well as delivering indicated therapy.

Following from the evaluation of block 320 is a decision block 322 wherein a determination is made whether the arrangement of one or more sensing/stimulation electrodes needs to be adjusted. In certain implementations, at initial implantation the positioning and/or fixation of one or more individual electrodes may need to be adjusted for improved sensing performance and/or more efficient delivery of therapy to the target tissue.

If the determination of the decision block 322 is affirmative, an adjustment block 324 follows wherein the electrodes are adjusted as appropriate. If the determination of block 322 is negative, e.g., that the current placement of sensing/stimulation electrodes is satisfactory, a block 326 follows.

In one embodiment, the block 326 comprises an evaluation of a current set of the multiple sensing/stimulation vectors at least at a rest state and at an elevated patient metabolic rate. As previously noted, a number of adjustable operational parameters are typically available in a given device 10. These parameters can include such variables as capture thresholds, stimulation amplitudes and durations, refractory periods, stimulation timing intervals, detection thresholds, amplifier gains, etc. Selection of appropriate programmed parameters will be understood by one of ordinary skill and generally depend on a particular configuration of device 10 as well as the particular needs of the given patient. Evaluation of operation of the device 10 along multiple spatial vectors and at rest an elevated metabolic rate provides increased flexibility to the clinician in adapting the therapy to the needs of the patient.

Following from the evaluation of block 326, the device 10 is programmed with a set of operating parameters that will generally include rate responsive parameters. Block 330 also includes designation of at least one cardiac performance indicator for ongoing evaluation of the performance of the device 10. In one embodiment, the cardiac performance indicator can include synchrony indicators, such as intervals or delays between electrical and/or mechanical indicators of the patient's cardiac performance, for example as indicated by the parameters 218, 220, 222, 224. In other embodiments, the cardiac performance indicator can include difference integrals between left ventricular and right ventricular impedance measurements as previously described with respect to FIG. 6. Yet other embodiments can include delays or intervals between peak impedance measures and/or peak impedance amplitudes. The designation of the at least one cardiac performance indicator in at least certain embodiments comprises designation of a cardiac performance indicator that can be self determined by the device 10 to facilitate closed loop programming of the device 10.

Following from block 330 occurs an ongoing determination block 340 wherein a determination is made during the implantation period whether or not the patient's physiologic performance, for example as indicated by the one or more cardiac performance indicators, suggests that adjustment or reprogramming of the operating parameters of the device 10 would improve performance thereof. In one embodiment, an elongation or increased delay between interventricular peak impedance measurements can trigger an adjustment of the devices 10 operating parameters. Similarly, in certain embodiments, a decrease in the sensed peak impedance amplitude below a determined threshold can likewise trigger a reevaluation of the device's programming 10. In certain embodiments, the evaluation of block 340 can proceed on a regular period basis, for example on a hourly, daily, weekly, etc. basis. The determination of block 340 can also be triggered asynchronously in certain embodiments, for example upon receipt of an appropriate command from an attending clinician provided via the external device 102.

When the determination of block 340 is negative, a block 342 follows wherein the device 10 continues to monitor the patient's condition and generate and deliver indicated therapy under the existing set of operating parameters. If, however, the determination of block 340 is affirmative, e.g., that a revised or reprogrammed set of operating parameters might provide improved physiologic performance, indicated adjustments are made in a block 344. As previously noted, in certain embodiments, the device 10 is configured such that the evaluation of block 340 and the adjustment of block 344 can proceed in a closed loop or self programming manner such that the device 10 is capable of automatically adjusting its own operation to provide optimized therapy to the patient. These embodiments provide the significant advantage of facilitating ongoing refinement of the device's operation without necessarily requiring the direct intervention of attending clinicians. This not only provides improved therapy delivery to the patient, but also reduces burden on the highly skilled and trained clinicians.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. An implantable cardiac stimulation device comprising:
   an implantable stimulation pulse generator adapted to generate therapeutic stimulation;
   at least one implantable lead defining at least one stimulation circuit and one sensing circuit adapted to sense at least one physiologic parameter indicative of a patient's physiological activity; and
   a controller in communication with the at least one lead said controller programmed to receive signals indicative of the patient's physiologic activity and with the stimulation pulse generator such that the controller can selectively induce delivery of the therapeutic stimulation and wherein the controller operates under a first programmed set of a plurality of variable operational parameters wherein the operational parameters define timing intervals under which the therapy is delivered and characteristics of the therapy delivered, and wherein the controller is further adapted to periodically evaluate signals indicative of the patient's cardiac activity for effectiveness of the therapy delivery in achieving improved synchrony between heart chambers as compared to a predetermined eucontractile performance for the patient, wherein the eucontractile performance is determined based on assessment of a plurality of patients each exhibiting similar physiology to the patient which indicates desired healthy activity at rest and at elevated metabolic levels for the patient and wherein the controller is further adapted to automatically self-reprogram the first set of operational parameters to a second set of operational parameters to improve effectiveness of the timing intervals of the therapy delivery to obtain improved synchrony between heart chambers as compared to the predetermined eucontractile performance for the patient.

2. The device of claim 1, wherein the controller is adapted to evaluate the signals indicative of the patient's cardiac activity for effectiveness of the timing intervals on a regular periodic basis.

3. The device of claim 1, wherein the controller is adapted to evaluate the signals indicative of the patient's cardiac activity for effectiveness of the therapy delivery upon triggering by a change in the observed cardiac performance.

4. The device of claim 1, wherein the signals indicative of the patient's cardiac activity are indicative of synchrony between heart chambers.

5. The device of claim 1, wherein the signals indicative of the patient's cardiac activity are indicative of peak amplitude of a transcardiac impedance signal.

6. The device of claim 1, wherein the signals indicative of the patient's cardiac activity correspond to impedance measurements of activity along different spatial vectors and wherein integrals of the impedance measurements over time are calculated as bounded by the signals along different vectors and wherein the patient's cardiac activity is evaluated at least partially based on differences of the integrals of the impedance measurements between different spatial vectors.

7. The device of claim 1, wherein the controller evaluates the signals indicative of the patient's cardiac activity by comparing the signals to a template of desired activity.

8. A therapeutic device system comprising:

an implantable therapeutic stimulation device comprising an implantable stimulation pulse generator adapted to generate therapeutic stimulation;

at least one implantable lead defining at least one stimulation circuit and one sensing circuit adapted to sense at least one physiologic parameter indicative of a patient's physiological activity; and a controller in communication with the at least one lead said controller programmed to receive signals indicative of the patient's cardiac activity and with the stimulation pulse generator such that the controller can selectively induce delivery of therapeutic stimulation under a set of a plurality of operational parameters that define interval timing characteristics and parameters for delivery of the therapy;

an external user interface adapted to display data and convert user inputs into control signals; and telemetry adapted for communication between the implantable stimulation device and the external user interface such that the external user interface can program an initial set of the operational parameters and wherein the controller is adapted to evaluate the patient's cardiac activity in order to achieve improved synchrony between heart chambers as compared to a predetermined eucontractile performance for the patient, wherein the eucontractile performance is determined based on assessment of a plurality of patients each exhibiting similar physiology to the patient which indicates desired healthy activity at rest and at elevated metabolic levels for the patient and autonomously closed-loop reprogram at least the interval timing parameters to improve delivery of the therapeutic stimulation for improved electromechanical synchrony between the chambers of the heart as compared to a predetermined eucontractile performance for the patient.

9. The system of claim 8, wherein the implantable device is adapted to compare the at least one physiologic parameter indicative of a patient's cardiac activity to predetermined desired values for the at least one physiologic parameter to determine if adjustment of the interval timing is indicated.

10. The system of claim 8, wherein the implantable device is further adapted to evaluate the patient's physiologic activity for indications of adjustment of the interval timing parameters based at least partially on a physiologic parameter that is not directly utilized for determination of therapy delivery.

11. The system of claim 10, wherein the implantable device is adapted to evaluate the patient's physiologic activity for indications of adjustment of the interval timing parameters based at least partially on transcardiac impedance measurements.

12. The system of claim 8, wherein the controller is adapted to evaluate the signals indicative of the patient's cardiac activity for effectiveness of the timing intervals on a regular periodic basis.

13. The system of claim 8, wherein the controller is adapted to evaluate the signals indicative of the patient's cardiac activity for effectiveness of the therapy delivery upon triggering by a change in the observed cardiac performance.

14. The system of claim 8, wherein the signals indicative of the patient's cardiac activity are indicative of peak amplitude of a transcardiac impedance signal.

15. The system of claim 8, wherein the signals indicative of the patient's cardiac activity correspond to impedance measurements of activity along different spatial vectors and wherein integrals of the impedance measurements over time are calculated as bounded by the signals along different vectors and wherein the patient's cardiac activity is evaluated at least partially based on differences of the integrals of the impedance measurements between different spatial vectors.

16. The system of claim 8, wherein the controller evaluates the signals indicative of the patient's cardiac activity by comparing the signals to a template of desired activity.

* * * * *